(12) United States Patent
Vidal et al.

(10) Patent No.: US 9,072,769 B2
(45) Date of Patent: Jul. 7, 2015

(54) WOLFBERRIES AND SKIN INFLAMMATION (75) Inventors: Karine Vidal, Lausanne (CH);
Stephanie Blum-Sperisen, Pully (CH);
David Philippe, Lausanne (CH); Olivier Ballevre, Beijing (CN); Peter Bucheli, Bremgarten bei Bern (CH); Junkuan Wang, Lonay (CH)

(73) Assignees: Nestec S.A., Vevey (CH); L'Oreal, Paris (FR)

( * ) Notice: Subject to any disclaimer, the term of this patent is extended or adjusted under 35 U.S.C. 154(b) by 921 days.

(21) Appl. No.: 12/677,488

(22) PCT Filed: Sep. 12, 2008

(86) PCT No.: PCT/EP2008/062132
§ 371 (c)(1),
(2), (4) Date: May 10, 2010

(87) PCT Pub. No.: WO2009/034165
PCT Pub. Date: Mar. 19, 2009

(65) Prior Publication Data
US 2010/0221372 A1 Sep. 2, 2010

(30) Foreign Application Priority Data
Sep. 12, 2007 (EP) .................................. 07116190

(51) Int. Cl.
*A61K 36/00* (2006.01)
*A61K 36/815* (2006.01)

(52) U.S. Cl.
CPC .................................. *A61K 36/815* (2013.01)

(58) Field of Classification Search
None
See application file for complete search history.

(56) References Cited

U.S. PATENT DOCUMENTS

| | | | |
|---|---|---|---|
| 2005/0113312 A1 | 5/2005 | Maeda et al. | 514/23 |
| 2006/0024339 A1* | 2/2006 | Murad | 424/401 |
| 2007/0065380 A1 | 3/2007 | Maeda et al. | 424/62 |
| 2007/0202195 A1 | 8/2007 | Wang et al. | 424/725 |
| 2008/0254152 A1 | 10/2008 | Barrett et al. | 424/728 |

FOREIGN PATENT DOCUMENTS

| | | |
|---|---|---|
| CN | 1100949 | 4/1995 |
| CN | 1135338 | 11/1996 |
| JP | 2007-176814 | 7/2007 |
| WO | WO 03/057707 A1 | 7/2003 |
| WO | WO 2005018656 | 3/2005 |
| WO | WO 2005/058314 A2 | 6/2005 |
| WO | WO 2005/092121 A2 | 10/2005 |
| WO | WO 2005092121 A2 * | 10/2005 |

OTHER PUBLICATIONS

Li et al, Effect of the *Lycium barbarum* polysaccharides on age-related oxidative stress in aged mice. Journal of ethnopharmacology, (May 22, 2007) vol. 111, No. 3, pp. 504-511.*
Wolber et al, Antioxidant status and role of oxidative stress in atopic dermatitis, Journal of Investigative Dermatology (1996) vol. 106, No. 4, pp. 888.*
European Search Report, Application No. EP 07116190 dated Feb. 12, 2008.
D. Gao et al., XP009095621, Effects of *Lycium barbarum*. L. Root Bark Extract on Alloxan-Induced Diabetic Mice, Future Medicine, Therapy, vol. 4, No. 5, pp. 547-553, (2007).
H. Eum et al, XP009095622, "Anti-Inflammatory Activity OfCML-1: An Herbal Formulation", The American Journal of ChineseMedicine, vol. 33, No. 1, pp. 29-40 (2005).
Notification of Transmittal of the International Search Report and the Written Opinion of the International Searching Authority, or the Declaration, PCT/EP2008/062132, mailed Jan. 19, 2009.
Etkin Nina L., (XP009095619) "International Symposium on *Lycium* Species", Journal of Ethnopharmacology, vol. 78, No. 1, p. 115 (2001).
Database FSTA/IFS abstract, (XP003603161) "International Food Information Service", (2007).
Communication from European Patent Office for Application No./Patent No. 08804097.7-2107/2200624 dated May 6, 2011.
Mohammad Azam Khan; Muheet-e-Azam, vol. I (19th century AD), Matba Nizami, Kanpur, 1896 AD p. 186; Formulation ID: MH3/161 Formulation Name: Akaara (2 pages).
Mohammad Najmul Ghani Khan; Khazaain-al-Advia, vol. II (20th century AD), Nadeem Yunus Printer/Sheikh Mohd Basheer & Sons, Lahore, 1911 AD p. 352; Formulation ID: AN2/333U; Formulation Name: Safoof-e-Chirchita Barae Waram (2 pages).
Mohammad Najmul Ghani Khan; Khazaain-al-Advia, vol. II (20th century AD), Nadeem Yunus Printer/Sheikh Mohd Basheer & Sons, Lahore, 1911 AD p. 353; Formulation ID: AN2/333GI; Formulation Name: Dawa-e-chirchita Barae Zaheer (2 pages).
Mohammad Najmul Ghani Khan; Khazaain-al-Advia, vol. III (20th century AD), Nadeem Yunus Printer/Sheikh Mohd Basheer & Sons, Lahore, 1926 AD p. 866; Formulation ID: JA6/826L; Formulation Name: Nuskha-e-zimaacl Barai Bars (2 pages).

* cited by examiner

*Primary Examiner* — Qiuwen Mi
(74) *Attorney, Agent, or Firm* — K&L Gates LLP (57) ABSTRACT

The present invention relates in general to the field of inflammation. In particular the present invention relates to the use of natural compounds for the preparation of a product to treat or prevent inflammation. For example an extract of wolfberry was shown to have anti-inflammatory properties. One embodiment of the present invention relates to the use of a primary composition comprising wolfberries or a part thereof for the preparation of a product to treat or prevent inflammation.

18 Claims, 7 Drawing Sheets

WOLFBERRIES AND SKIN INFLAMMATION

This application is a 371 filing of International Patent Application PCT/EP2008/062132 filed Sep. 12, 2008.

BACKGROUND

The present invention relates in general to the field of inflammation of the skin. In particular the present invention relates to the use of natural compounds for the preparation of a cosmetic and/or dermatological composition for a topical use or as a food supplement, intended more particularly for the prevention and/or the treatment of inflammation of the skin and related disorders. For example an extract of wolfberry was shown to have anti-inflammatory properties.

Inflammation is the complex biological response of tissues to harmful stimuli, such as pathogens, damaged cells, or irritants. It is generally a protective attempt by the organism to remove the injurious stimuli as well as initiate the healing process for the tissue. However, insufficiently regulated inflammation can lead to several diseases irrespective of the age of the subject.

Ageing is associated with a dysregulation of the immune system, such as a noted decline in cell-mediated immune response concomitant with an increased humoral immune dysfunction (e.g. lower response to vaccine). Aging is furthermore often associated with a status of low-grade inflammation. Consequently, in particular many elderly subjects are at increased risk of infectious and non-infectious diseases that contribute to morbidity and mortality.

Wolfberry is already known for its multiple health benefits, based on is multi-nutrients (e.g. zeaxanthin, vitamins and *Lycium barbarum* polysaccharides) composition.

However, there remains a need in the art to have available natural compounds that have anti-inflammatory properties.

For example, nutritional intervention such as with n-3 PUFA (poly unsaturated fatty acid) diminished inflammatory cell functions, but also decreased cell-mediated immune response (e.g. lymphocyte proliferation and NK activity), which can lead to potential detrimental effects with regard to the host defence.

Hence it was the object of the present invention to provide the art with an alternative natural compound that has anti-inflammatory properties and that does not have any detrimental effects with regard to the subject's immune defence.

SUMMARY OF THE INVENTION

The present inventors were surprised to find that a wolfberry extract has anti-inflammatory properties. Consequently the object of the present invention was achieved by providing the art with a use of a wolfberry extract to prepare a topical cosmetic and/or dermatological composition or a food supplement to treat and/or prevent inflammation of the skin and related disorders. It was also found that the immune response was maintained.

Consequently, one embodiment of the present invention is the use of a primary composition comprising wolfberries or a part thereof and optionally milk or a milk-protein containing carrier for the preparation of a product to treat and/or prevent inflammation.

The cosmetic and/or dermatological product may be intended for topical administration or oral administration as a food supplement.

The milk or milk protein can be derived from animal or plant origin, or from mixtures thereof. Preferably, the milk is cows milk, lama milk, buffalo milk, goat milk, sheep milk, vegetable milk, in particular soy milk or a mixture thereof. Milk protein is to be understood as a protein fraction obtainable from one or more of the milk types listed above.

Preferably, the primary composition is a miscible composition.

Advantageously, in particular if the primary composition comprises milk or a milk-protein containing carrier, it has a close profile of the essential active components of whole wolfberries, it has a good stability, miscibility and/or dispersibility in aqueous systems.

Moreover, in particular if comprising milk or a milk-protein containing carrier, the primary composition has an enhanced nutritional value, in the form of a better bioavailability and stability. It has a pleasant taste and colour. It can be used directly or concentrated or dried into powder for several applications into daily-consumed food products or other nutritional uses.

All these features can be achieved if the primary composition is prepared by a process for preparing the primary composition to deliver the essential lipophilic and/or hydrophilic bioactive components of wolfberries comprising the steps of: i) mixing and milling wolfberry material in milk or milk protein-containing liquid medium, ii) optionally separating insoluble fibers to obtain an aqueous suspension iii) optionally pasteurising the resulting suspension iv) optionally add synthetic or natural bioactive components during the processing v) and further optionally drying the suspension to obtain a powder.

Consequently, in one embodiment of the present invention the primary composition is obtainable by a process comprising the steps of: i) mixing and milling wolfberry material in milk or milk protein-containing liquid medium, ii) optionally separating insoluble fibers to obtain an aqueous suspension iii) optionally pasteurising the resulting suspension iv) optionally add synthetic or natural bioactive components during the processing v) and further optionally drying the suspension to obtain a powder.

This process has the major advantage of being natural and cost effective enabling improved delivery of multi-nutrients in the form of a combination of stabilized water- and fat-soluble compounds in their natural compositions, free of organic solvent residues.

In a further aspect, the invention provides a method for increasing miscibility or dispersibility in an aqueous system, stability, and bioavailability of bioactive compounds of wolfberry material using a process as described above, in particular, by using milk or milk proteins, soy milk or milk-like proteins from plants for extracting and delivering the multi-nutrients of functional ingredients of wolfberries.

DETAILED DESCRIPTION OF THE INVENTION

A primary composition as described above can be used for delivering the multi-nutrients of functional ingredients of wolfberries with improved bioavailability, miscibility and stability.

The term bioactive compound is to be understood to mean molecules or components showing a biological activity or a health impact when orally or topically applied.

Wolfberries may be used, e.g., in the form of fruits and other parts of the plant. Fruits may be used in the form of fresh, concentrated or dried materials, for example, air or freeze dried material. It is however preferred to use dried ripe fruit.

In a preferred embodiment of the present invention the primary composition comprises at least a part of the essential lipophilic and/or hydrophilic bioactive components of wolfberries.

The essential lipophilic and/or hydrophilic bioactive components are preferably selected from the group consisting of lipids, alkaloids, proteins, carbohydrates, glycoproteins, carotenoids, polyphenolic compounds such as flavonoids, vitamins, minerals, or mixtures thereof.

The carotenoids may be selected from the group consisting of carotenes and xanthophylls such as lycopene, carotene, phytofluene, phytoene, canthaxanthin, beta-cryptoxanthin, capsanthin, lutein, zeaxanthin, or those in the form of fatty acid esters, or mixtures thereof.

The glycoproteins are preferably selected from the group consisting of arabinogalactan proteins, in particular *Lycium barbarum* polysaccharide and macromolecules that can be detected by the beta-glucosyl Yariv reagent.

The flavonoids are preferably selected from the group consisting of flavones such as apigenin, luteolin or diosmetin, flavonols such as quercetin, myricetin, kaempferol, flavanones, anthocyanidins such as pelargonidin, malvidin, or isoflavones such as genistein, daidzein, or mixtures thereof.

The primary composition of the present invention may contain at least the essential bioactive components of wolfberries or a part thereof, excluding insoluble fibres, in a milk or milk protein-containing carrier. The milk carrier may be in the form of skimmed milk or whole milk from animal or plant origin (e.g. soy milk, juice or coconut milk, etc.). In a more preferred embodiment, cow's milk or soy milk are used, depending on the primary composition which is desired. The milk-containing carrier may be any edible liquid containing milk proteins such as caseins or whey proteins, for example.

Vegetable oils may optionally be added to the liquid medium.

The wolfberry material may be mixed and milled in said milk or milk protein-containing liquid medium in a respective ratio of about 1:1 to 1:1000, preferably from 1:5 to 1:50. The mixing and milling step may be carried out at a temperature of from 1 to 95° C., preferably from about 20 to 80° C. and more preferably from 40 to 80° C. Then, insoluble fibres may be at least partially removed to obtain an aqueous suspension.

This can be done by any conventional method. The resulting primary composition may be further pasteurized and/or dried into a powder by techniques known in the art. The primary composition obtained may also be in liquid or gel form.

The present invention thus provides a primary composition having a similar profile of the important nutrients as the whole fruit, it has a good stability, miscibility and bioavailability. These compositions may be highly dispersible in an aqueous system, if the powder form is chosen. In this case, the powder is dispersible in cold or hot water, for example. It can equally well be added in milk.

The composition may additionally comprise one or more of emulsifiers, stabilizers, antioxidants and other additives. Use is preferably made of emulsifiers compatible in food, such as phospholipids, for example lecithin, polyoxyethylene sorbitan mono- or tristearate, monolaurate, monopalmitate, mono- or trioleate, a mono- or diglyceride.

Use may also be made of any type of stabilizer that is known to be usable in food supplements, in cosmetics or in pharmaceuticals.

Use may be made of any type of antioxidants that is known to be usable in food supplements, in cosmetics or in pharmaceuticals.

Use may be further made of additives, of flavourings, of colorants known to be usable in food supplements, cosmetics or pharmaceuticals.

The emulsifiers, stabilizers, antioxidants and additives may be added in accordance with the intended final use of the primary composition.

The composition may further contain synthetic or natural bioactive ingredients such as amino acids, fatty acids, vitamins, minerals, carotenoids, polyphenols, etc. that can be added preferably either by dry or by wet mixing to said composition before pasteurization and/or drying.

The product prepared by the use of the present invention may be a dietary or food supplement, a supplement to be used as or in a medicament or a supplement to be used as or in a cream.

In a preferred embodiment of the present invention the product is intended for use by and/or application to humans or pets.

The product can be administered to subjects of any age, in particular infants, children, adolescents, adults and/or elderly. However, the benefits of wolfberries appear to be in particular well suited for adults and the elderly.

According to a preferred embodiment of the present invention the product prepared by the use of the present invention is intended for human consumption.

Accordingly, the primary composition may be an additive in a food supplement for oral administration, or in a product for topical application such as cosmetics or pharmaceutical products.

If the product is a nutritional supplement for oral administration it may be present in capsules, gelatin capsules, soft capsules, tablets, sugar-coated tablets, pills, pastes or pastilles, gums, or drinkable solutions or emulsions, a syrup or a gel. The dose of the primary composition may be varied depending on the intended purposes by those of skill in the art but will generally be between about 0.1 to 100 weight-% of the primary composition. Such a supplement might also include a sweetener, a stabilizer, an antioxidant, an additive, a flavouring agent and/or a colorant. A supplement for a cosmetic purpose might additionally comprise a compound active with respect to the skin.

In another embodiment, if the product of the present invention is a pharmaceutical cosmetical composition it can be administered for prophylactic and/or therapeutic treatments.

In therapeutic applications, compositions are administered in an amount sufficient to at least partially cure or arrest the symptoms of the disease and its complications. An amount adequate to accomplish this is defined as "a therapeutically effective dose". Amounts effective for this purpose will depend on a number of factors known to those of skill in the art such as the severity of the disease and the weight and general state of the patient. In prophylactic applications, compositions according to the invention are administered to a patient susceptible to or otherwise at risk of a particular disease in an amount that is sufficient to at least partially reduce the risk of developing a disease. Such an amount is defined to be "a prophylactic effective dose". Again, the precise amounts depend on a number of patient specific factors such as the patient's state of health and weight.

The compounds of the invention if administered as a pharmaceutical composition are preferably administered with a pharmaceutically acceptable carrier, the nature of the carrier differing with the mode of administration, for example, enteral, oral and topical (including ophthalmic) routes. The desired formulation can be made using a variety of excipients including, for example, pharmaceutical grades of mannitol, lactose, starch, magnesium stearate, sodium saccharin, cellulose, magnesium carbonate.

It will be appreciated that the skilled person will, based on his own knowledge select the appropriate components and galenic form to target the active compound to the tissue of interest, e.g. the skin, colon, stomach, eyes, kidney or liver, taking into account the route of administration.

The invention also relates to a cosmetic composition comprising the primary composition described above. It may be formulated in lotions, shampoos, creams, sun-screens, after-sun creams, anti-ageing creams and/or ointments, for example. This composition which can be used topically additionally comprises a fat or an oil which can be used in cosmetics, for example those mentioned in the CTFA work, Cosmetic Ingredients Handbook, Washington. It is also possible to add other cosmetically active ingredients. The composition additionally comprises a structuring agent and an emulsifier. Other excipients, colorants, fragrances or opacifiers can also be added to the composition. It will be appreciated that the present cosmetic products will contain a mixture of different ingredients known to the skilled person, ensuring a fast penetration of the said substance into the skin and preventing degradation thereof during storage.

Administering a nutritional supplement or a cosmetic or pharmaceutical composition as described above, results in an improved health, in particular by at least partially reducing inflammation.

The inflammation that can be treated by applying the product prepared by the use of the present invention can be selected from the group consisting of skin inflammations and related disorders such as burns, such as UV or chemical-induced skin inflammation, eczema, reactive skin, psoriasis, vitiligo, acne, atopic dermatitis and skin imperfections.

The reactivity of the skin is a response of the skin to specific compounds (synthetic or natural) or environmental factors (UV, pollution, cold . . . ) that applied to or in contact with the skin surface induce more often skin redness, pain, of smarting, tightness and leads to important discomfort.

Then following irritation, skin reacts to restaure the impaired cutaneous homeostasis and repairs the induced damages. The skin response may be infra-clinical. However, this response of skin tissue is very uncomfortable for the subject in contact with irritating agent.

When irritants reach the skin, they can induce an irritating effect by themselves but they can also react with some substances present in cells of tissues and then release other substances such as cytokines. These cytokines can act in the skin to increase the inflammatory response and/or recruit other blood cells involved in the inflammatory process. At the end, this inflammatory cascade leads to a reaction of the skin, mainly skin irritation. According to the quality and the quantity of the irritating agent, subjects can have some discomforts such as skin warming, of smarting, tightness, itching and/or skin redness, oedema.

Figure 1:
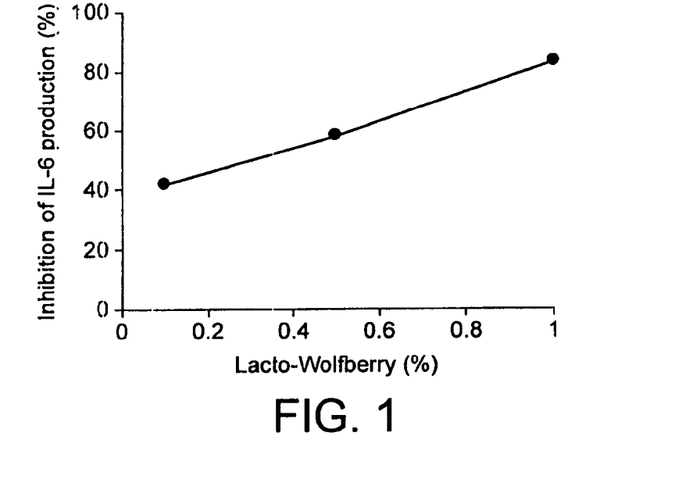
FIG. 1 shows the inhibition of LPS-mediated IL-6 production by LWB in the murine macrophage cell line (RAW cells).
Figure 9A:
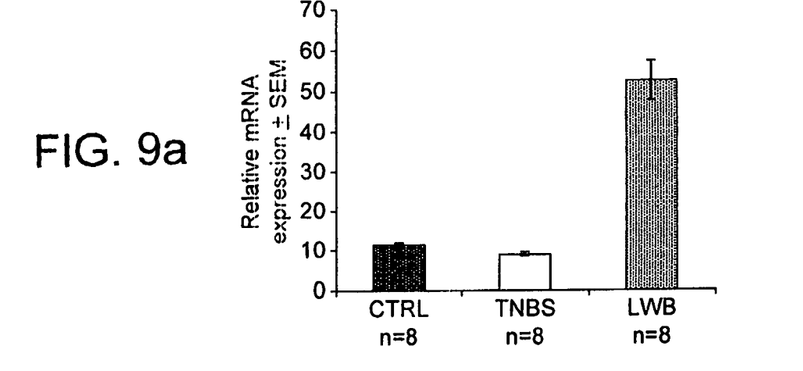
FIG. 9 shows the expression of anti-oxidant genes such as GPX-1, CAT1 and SOD2 in a murine model of acute intestinal inflammation without and with supplementation of LWB.
Figure 9B:
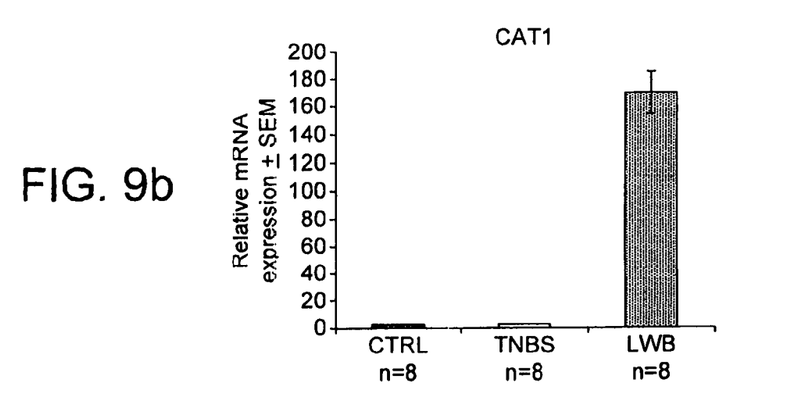
Figure 9C:
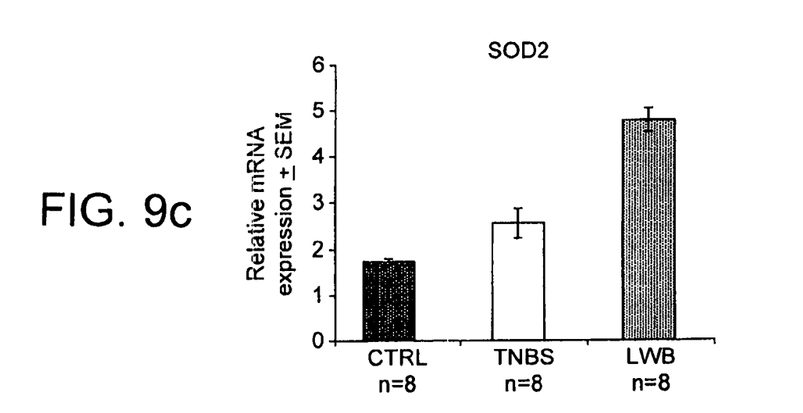
Figure 10A:
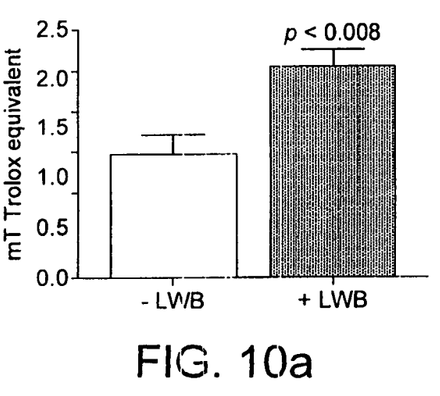
FIG. 10 shows the anti-oxidant capacity. Right panel: Mean+/− SEM; Left panel: Individual values and median
Figure 10B:
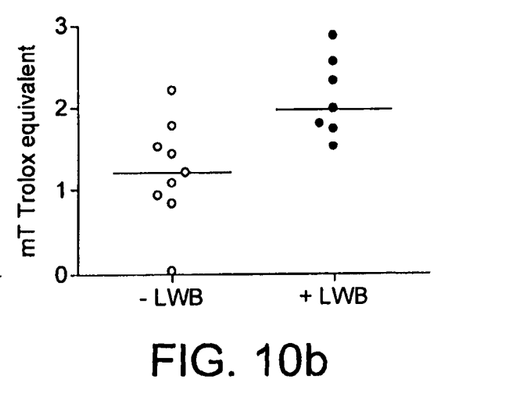
Figure 11:
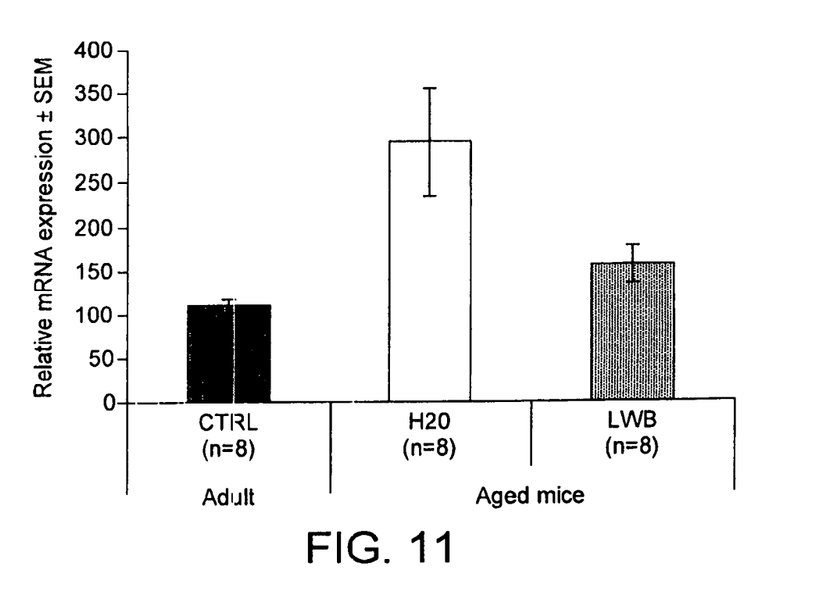
FIG. 11 shows the expression of the gene encoding for TNF-α in the liver of aged mice supplemented with LWB compared to the levels observed in the liver of normal aged mice (H20) and adult mice (CTRL).
Figure 12:
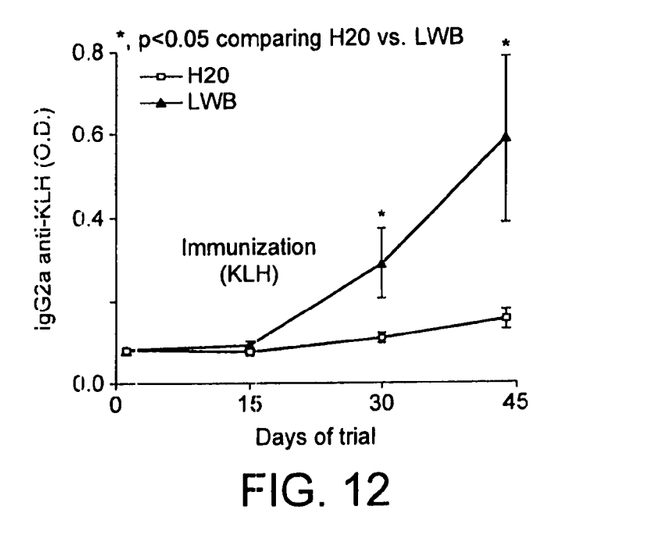
FIG. 12 shows the antigen (KLH)-specific antibody response in aged mice.
Figure 13:
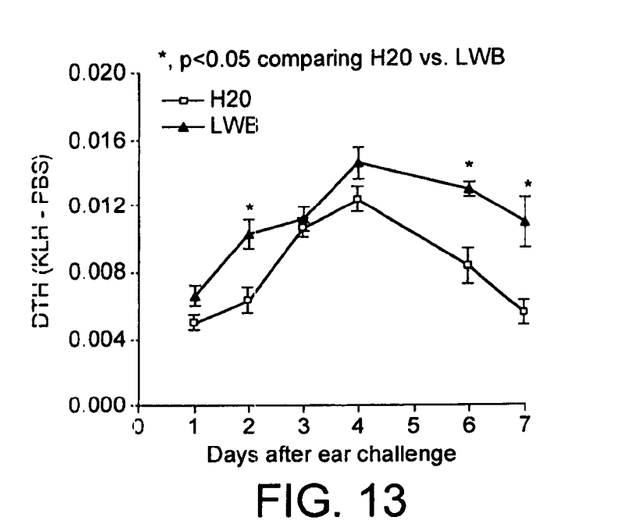
FIG. 13 shows the cell-mediated immune delayed-type hypersensitivity (DTH) response in aged mice.

The present inventors have investigated the molecular mechanism of the anti-inflammatory effect primary composition of the present invention. Without wishing to be bound by theory the inventors presently believe that it suppresses the LPS-mediated pro-inflammatory cytokine production by macrophages (FIG. 1) and TNF-α- or LPS-induced NF-κB activation (FIG. 2) pathway in human intestinal epithelial cells. In preclinical studies, dietary supplementation with the primary composition of the present invention demonstrated strong anti-inflammatory properties in a murine model of acute intestinal inflammation (FIGS. 3 to 10). In addition, the primary composition of the present invention was further capable of reducing the expression of pro-inflammatory cytokines, such as TNF-α, in the liver of aged mice (FIG. 11). Furthermore, dietary supplementation with the primary composition of the present invention enhanced antigen-specific humoral and cell-mediated immune responses in aged mice (FIGS. 12 and 13, respectively). Thus, primary composition of the present invention was shown to be beneficial in reducing the inflammatory status. At the same time, the primary composition of the present invention further is capable of supporting the immune system.

Consequently, the product prepared by the use of the present invention can be used to reduce the inflammatory status and—simultaneously—to boost the immune system.

Hence, the primary composition of the present invention has the potential to bring the impaired immune and inflammatory response back to homeostasis. By this dual effect, the primary composition of the present invention is, e.g., suitable for the use in products for elderly.

In particular the primary composition of the present invention is beneficial in maintaining the immune function during ageing while reducing the age-related low-grade inflammatory status of the skin.

Additionally, the primary composition and/or the cosmetic or dermatological product of the present invention may be used treat or prevent disorders related to oxidative stress. The inventors have shown that the application of the primary composition and/or the product of the present invention can induce a strong increase of anti-oxidant genes such as GPX-1, CAT1 and SOD2 (FIG. 9). Consequently, the primary composition and/or the product of the present invention may provide protection against oxidative stress, caused for example by free radicals, such as •O2—, the superoxide anion; $H_2O_2$, hydrogen peroxide; •OH, the hydroxyl radical; ROOH, organic hydroperoxide; RO•, alkoxy radicals; ROO•, peroxy radicals; HOCl, hypochlorous acid; OONO—, peroxynitrite; and/or NO•.

It is clear to those of skill in the art that it is possible to freely combine any features described herein without departing from the scope of the present invention as originally disclosed.

BRIEF DESCRIPTION OF THE DRAWINGS

Further advantages and features of the present invention will be apparent from the following examples and figures.

EXAMPLES

Example 1

Preparation of a Primary Composition Comprising Wolfberries and Milk (LWB, Lacto-Wolfberry)

Dried wolfberry fruits (40 g) and whole milk (300 g) were introduced in a 1-liter container. The mixture was kept to stand for 10 minutes and treated with Polytron (Dispersing and Mixing Technology by KINEMATICA, PT3000) at 26000 rpm for 15 minutes under a nitrogen atmosphere. During the Polytron-treatment the temperature of the mixture was maintained at 80-85° C. by means of water bath and cooled to room temperature afterwards. The resulting mixture was then centrifuged at 2000 G for 10 minutes. The solid residue is discarded. The liquid phase (306 g of orange-yellow milk) was freeze dried. The dried product is finally grinded to give 54 g of orange-yellow powder, which had shown very god water-dispersible property and improved stability of zeaxanthin compared to wolfberry fruit powder.

Example 2

Reagents

Lacto-Wolfberry (LWB) powder from the pilot batch N° WB03A1506H produced at the NRC (Nestlé Research Center; Lausanne) as described above and Wolfberry extract powder (batch N° WB03A1506H) were provided by J. Wang (FS, Lipids & Bioactives). Lipopolysaccharide (LPS) from *E. coli* serotype 055:B5 was purchased from Sigma (St. Louis, Mo.). Human breast milk (HM) was collected from different healthy donors at 20 days post partum following ethical committee approval. Keyhole Limpet Haemocyanin (KLH) was purchased from Sigma.

Cell Culture

The mouse monocyte/macrophage cell line RAW 264.7 (TIB-71 from ATCC, Manassas, Va., USA) was maintained in Dulbecco's modified Eagle medium (DMEM, Amimed, Bioconcept, Allschwill, Switzerland) supplemented with 10% heat-inactivated FCS (Amimed) and 1% Penicillin/Streptomycin (Invitrogen, Paisley, UK) at 37° C. in a 5% $CO_2$/air incubator. Cells were sub-cultured using trypsin/EDTA (Sigma, St-Louis, Mo., USA). The human colonic adenocarcinoma cell line HT-29 clone 34 cells (i.e. HT-29 cells stably transfected with a NF-B reporter gene) were maintained in high glucose (4.5 g/l) DMEM (Bioconcept, Allschwill, Switzerland) containing 1% stable L-glutamine and supplemented with 10% heat-inactivated (one hour at 56° C.) FCS, 1% penicillin/streptomycin (Sigma, St Louis, Mo.), 500 μg/ml of G418 (Invitrogen) and 100 μg/ml of Normocin (Invivogen) at 37° C. in a 5% $CO_2$/air incubator. Culture medium was changed every 2 days until the cell monolayers reached ~90% confluence. Cells were sub-cultured using trypsin/EDTA (Sigma).

Quantification of LPS-Mediated IL-6 Expression

RAW 264.7 cells were seeded at $10^4$ cell/well in 96-flat bottom well plates (Nunc, Rosklide, Denmark) in normal culture medium at 37° C. in a 5% $CO_2$/air incubator. After 3 days of culture (i.e. cells reaching ~80% of confluence), cells were stimulated or not with 0.5 μg/ml *E. coli* LPS (055:B5, Sigma) in the absence or the presence of LWB samples (0.1-1% final concentration) for 24 hours in normal culture media. Cell culture supernatants were then harvested and used to quantify IL-6 production. Interleukin-6 (IL-6) levels in cell culture supernatant were determined by ELISA (Murine IL-6 Eli-pair, Diaclone, Besancon, France) according to manufactor's instructions.

NF-κB Activity

HT-29 clone 34 cells were seeded at $10^4$ cell/well in 96-flat bottom well plates (Nunc) in culture maintenance media. After 3-4 days of culture (i.e. cells reaching ~80% confluence), cells were washed in phosphate buffer saline (PBS) (Sigma) and then stimulated or not with LPS (10 ng/ml+5% human milk) or recombinant TNF-α (10 ng/ml; R&D systems, Oxon, England) in the absence or the presence of LWB samples for 24 hours in DMEM containing 1% penicillin/streptomycin. Cell culture supernatants were then harvested and stored at +4° C. O/N until analysis of NF-κB activity. Following NF-κB activation, HT-29 clone 34 cells secrete alkaline phosphatase (SEAP) in the culture supernatant. SEAP release was measured using a fluorescence detection method (Phospha-Light™ System) following the manufacturer's instruction (Applied Biosystems, Bedford, USA). Briefly, cell culture supernatants were incubated with reaction buffer from Phospha-Light™ System for 20 min in a white 96-well flat bottom polypropylen plate (Greiner) and luminescence was measured using the Spectrafluor Plus spectrometer (Tecan 8634 Hombrechtikon, Switzerland). Results are expressed as relative luminescence units (RLU).

TNBS-Induced Colitis Model

The TNBS colitis model is a model of acute inflammation induced by the chemical product: trinitrobenzene sulphonic acid (TNBS) at the dose of 150 mg/kg. Ten mice per group have been fed with diet containing 1% of LWB (50 mg) seven days before colitis induction and until sacrifice. From day 1 to day 4 after TNBS administration, 50 mg of LWB have been given by gavage to compensate for the lower food intake associated with acute intestinal inflammation. For each animal body weight loss, macroscopic, histological score, COX-2, pSTAT3, pro-inflammatory and anti-oxidant genes expression and anti-oxidant power were assessed. Macroscopic and histological score were performed following the scoring criteria of Wallace (Wallace et al, 1989) and Ameho (Ameho et al, 1997). COX-2, the inducible form of cyclooxygenase, a 72 kDa protein, is responsible for the inducible biosynthesis of prostaglandins under acute inflammatory conditions. Stat3 is a key signalling molecule for many cytokines; in particular for pro-inflammatory cytokines as IL-6.

Study Design for Assessing Immune Modulation in Aged Mice

Specific pathogen-free male C57BL/6J mice (4-weeks old) were purchased from Charles River Laboratories Inc. (France). Mice were housed under conventional circumstances (12 hours light/dark cycle, temperature 22° C., humidity 56%) and received water and semi-synthetic Kliba 3434 diet ad libitum. Until the age of 5 months, mice were maintained at 5 per cage and then they were individually caged. All conditions and handling of the animals were approved by the Nestlé and state ethical committees with the agreement of the Swiss Federal Veterinary Advisor. At 21-months old mice were randomised into 2 groups of 10 animals. Control non-supplemented mice (H20, n=10 per age group) and LWB-supplemented mice (LWB, n=10 per age group) received a semi-synthetic diet (AlN-93). LWB was provided as a 0.5% (w/v) solution in the drinking water, which was freshly prepared and changed every other day. During the trial (44 days), all mice were allowed to drink and eat ad libitum. The same study design was performed twice and also performed with 8-months old mice (n=8 per group). To study the in vivo T cell-dependent humoral response (antigen-specific antibody production) aged mice were immunized on day 15 of the trial by subcutaneous injection (100 μl) of an inert antigen Keyhole Limpet Haemocyanin (KLH, Sigma) at 100 μg in 1% Alum (Brenntag Biosector, Frederikssund, Denmark). The DTH response was used as an in vivo measure of cellular immunity. Measurements of ear thickness (ear swelling) taken prior to, and 24 hours to 8 days following, elicitation allowed for determination of the ability to generate a DTH response. Briefly, 7 days after immunisation of the mice with KLH (i.e. day 22 of trial), DTH responses were elicited by injecting the recall-antigen KLH (10 μl of 0.5 μg/ml) into each mouse's right ear. The left ears were injected with vehicle alone (saline=PBS) and served as internal controls for each animal. At 24 hours post-elicitation, and during the following 7 days, both the non-elicited (left ear) and the elicited ears (right ear) were measured. DTH responses (KLH-PBS) were expressed as the magnitude of ear swelling, i.e. the change in ear thickness using the following formula: Δ in ear thickness−[elicited ear (right, KLH) ear sickness−non-elicited (left, PBS) ear sickness], where Δ in ear thickness=[post-elicitation−pre-elicitation ear thickness]. Blood samples were collected on days 0, 15, 29 from the tail vein and on day 44 via cardiac puncture. Mice were sacrificed on day 44 of trial. At the autopsy, the liver was removed and a piece was immediately frozen in liquid nitrogen. Samples were stored at +80° C. until further analysis.

Quantification of KLH-Specific IgG2a Antibody Levels

Amounts of KLH-specific IgG2a antibodies in the sera were determined by ELISA. Briefly, microtiter plates were coated with KLH (50 μl/well at 100 ng/ml) and incubated at 37° C. during 3 hours. Free binding sites were blocked with ELISA buffer for 1 hour at 37° C. Samples were then added and incubated at +4° C. overnight. Bound antibodies were reacted 1 hour at 37° C. while shaking with a biotin-conjugated goat anti-mouse IgG2a (γ2a chain specific) from Southern Biotechnologies (Birmingham, USA). Plates were read at 450 nm after the addition of the TMB peroxydase substrate from KPL. Anti-KLH IgG2a antibody levels were expressed as means $OD_{450\,nm}$ values.

Genes Expression

Liver samples were transferred into 1 ml of RNA lysis buffer (Macherey-Nagel, Düren, Germany) and homogenized using Ribolyzer (Hybaid, Waltham, Mass., USA) with the following setting: power at 6 for 20 seconds. RNA extraction was conducted using a commercially available kit (NucleoSpin RNA II Kit; Macherey-Nagel, Düren, Germany). RNA quantification was achieved using the Ribogreen RNA Quantitation Kit (Molecular Probes; Eugene, Oreg. USA), and RNA quality was assayed using Agilent RNA 6000 Nano LabChip Kit (Agilent Technologies, Palo Alto, USA). Total RNA (2 μg) was reverse transcribed using Multiscribe reverse transcriptase following manufacturer's instructions (Applied biosystems, Biosystems; Rokreutz, Switzerland). Custom-made low density arrays (LDA) with 48 TaqMan probes (loading capacity: 8 samples per card in technical monoplicates) were purchased from Applied Biosystems (Foster City, USA) and used according to manufacturer instruction's. Gene expression was calculated using the relative quantification method ΔΔCt method with SDS 2.2.2 software (Applied Biosystems). The resulting cycle threshold (Ct) values were exported into MS Excel (Microsoft, USA) for further analysis. Briefly, the ΔCt value (i.e. Ct value of the target gene—Ct value of the GAPDH housekeeping gene) was first calculated and then the relative mRNA expression was determined using the following formula:

$$2^{-\Delta Ct} \times 10^6.$$

General Statistical Analysis

Data were analysed by means+/− SEM or SD, and the Student's T test (unpaired) or two-way ANOVA when appropriate. Probability values of less than 5% were considered as significant.

Results

Figure 2:
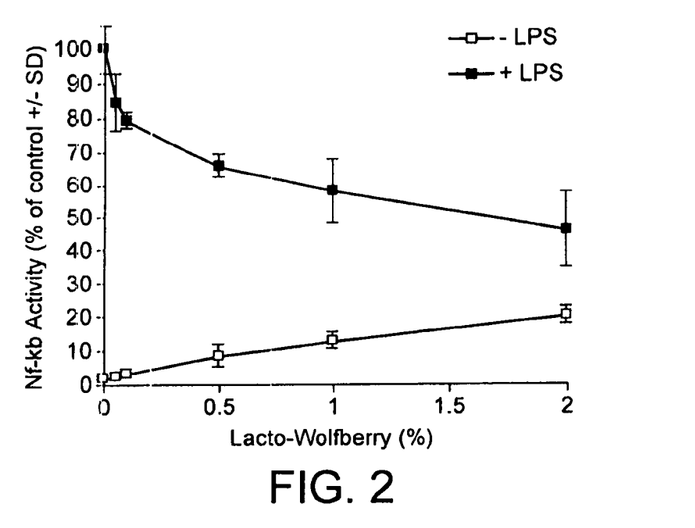
FIG. 2 shows the inhibition of LPS-mediated NF-κB activation by LWB in human intestinal epithelial cell line (HT-29 stably transfected with a NF-κB reporter gene)
Figure 3:
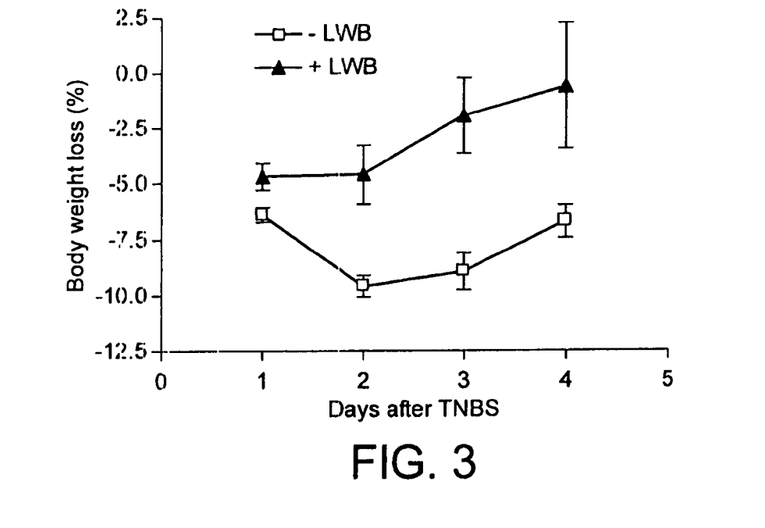
FIG. 3 shows the body weight loss after TNBS administration. Mean+/−SEM
Figure 4A:
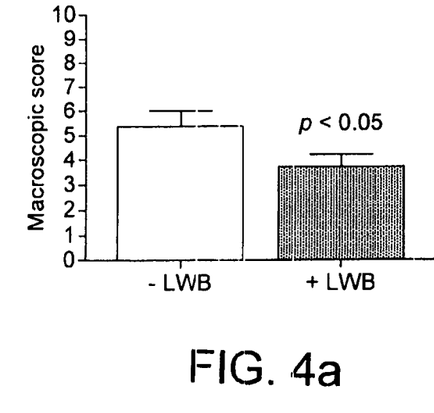
FIG. 4 shows the macroscopic score evaluation. Right panel: Mean+/− SEM; Left panel: Individual values and median
Figure 4B:
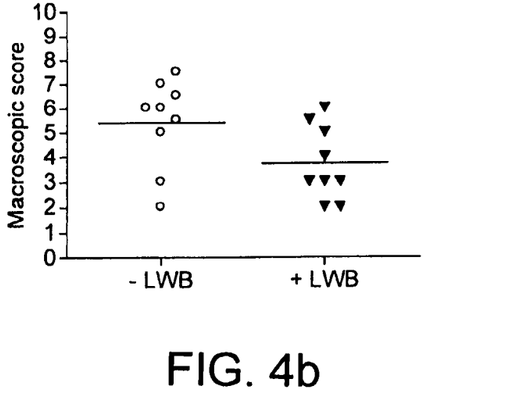
Figure 5A:
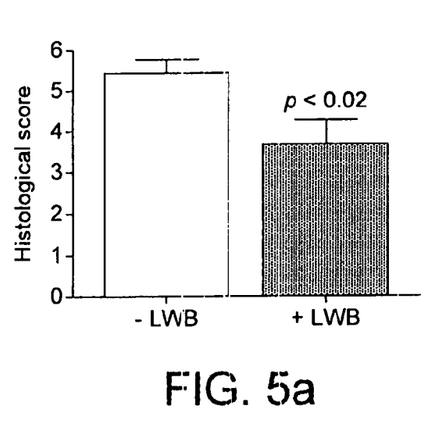
FIG. 5 shows the histological score evaluation. Right panel: Mean+/− SEM; Left panel: Individual values and median
Figure 5B:
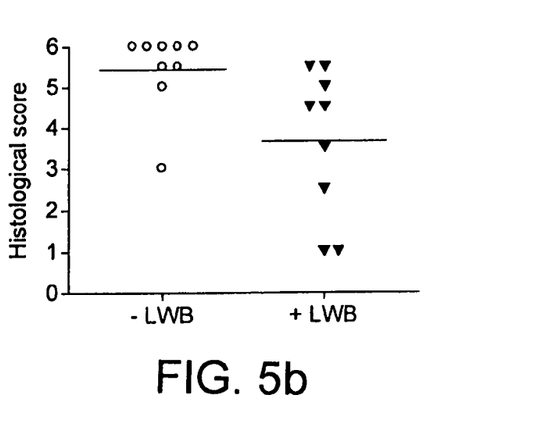

A) In vitro Experiments Demonstrating Anti-Inflammatory Properties of Lacto-Wolfberry Solution of Lacto-Wolfberry (LWB) inhibited in vitro the LPS-mediated release of the pro-inflammatory cytokine IL-6 by a murine macrophage cell line (FIG. 1) and LPS-mediated NF-κB activation in human intestinal epithelial cells (FIG. 2).

Figure 6A:
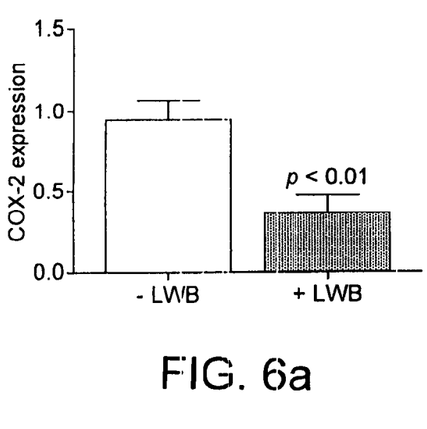
FIG. 6 shows the ratio of COX-2 on reference protein (actin). Right panel: Mean+/− SEM; Left panel: Individual values and median
Figure 6B:
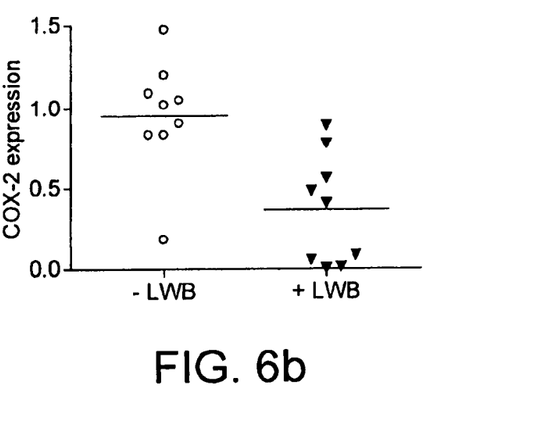
Figure 7A:
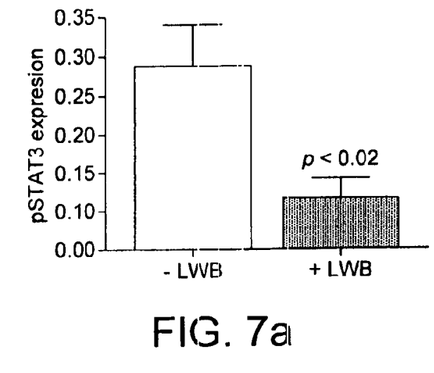
FIG. 7 shows the pSTAT3 expression. Right panel: Mean+/− SEM; Left panel: Individual values and median
Figure 7B:
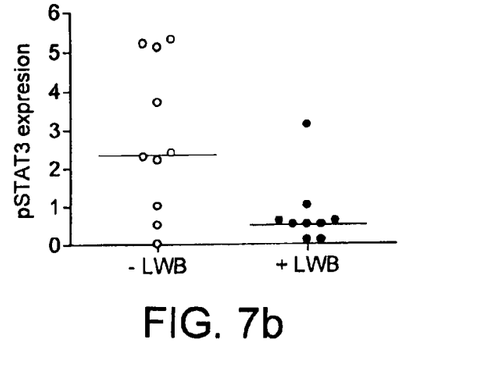
Figure 8A:
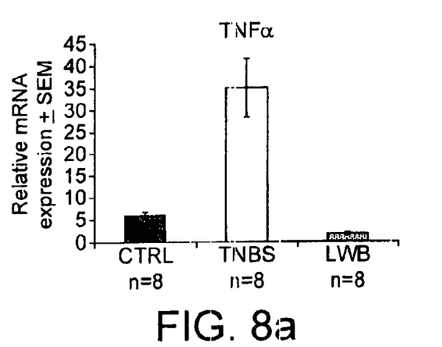
FIG. 8 shows the expression of pro-inflammatory genes, such as TNFα, IL-6 and IL-1β and proteins such as KC in a murine model of acute intestinal inflammation without and with supplementation of LWB.
Figure 8B:
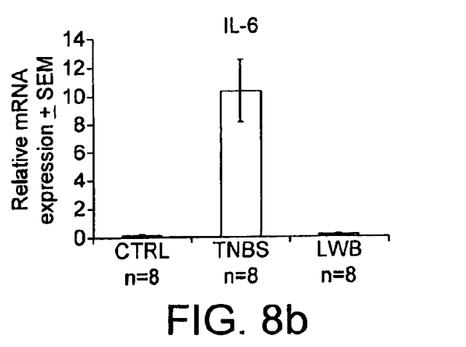
Figure 8C:
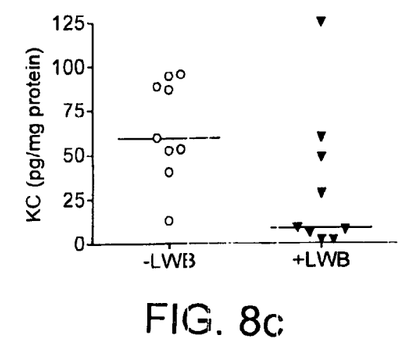
Figure 8D:
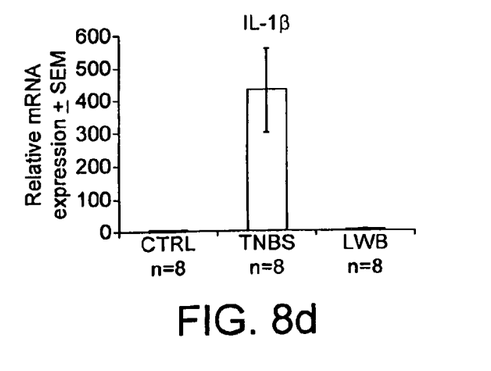

B) In vivo Experiments Demonstrating Anti-Inflammatory and Immune-Enhancing effects of Lacto-Wolfberry a. Pathological acute inflammation Dietary supplementation with LWB demonstrated strong anti-inflammatory properties in a murine model of acute intestinal inflammation. Oral administration of 1% LWB resulted in an improvement of body weight loss (FIG. 3), macroscopic and histological lesions (FIGS. 4 and 5), significant reduction of COX-2 and pSTAT3 expression levels (FIGS. 6 and 7). In addition, expression of pro-inflammatory genes, such as TNFα, IL-6 and IL-1β and proteins such as KC in the colon were reduced compared to the control group (FIG. 8). In parallel, LWB induced a strong increase of anti-oxidant genes such as GPX-1, CAT1 and SOD2 (FIG. 9) in the colon and increased anti-oxidant defenses in the plasma (FIG. 10).

b. Physiological aged-related low-grade inflammation

Dietary supplementation with LWB (0.5% in drinking water) induced a reduction of expression of inflammation-related genes in the liver of aged mice to levels observed in adult mice (FIG. 11: as an example, gene encoding for TNF-α).

c. Immune enhancing effect in aged mice

Dietary supplementation with LWB (0.5% in drinking water) improved both humoral (FIG. 12) and cell-mediated immune response (FIG. 13) in aged mice.

What is claimed is:

1. A method for treating inflammation, the method comprising:
   orally administering to an elderly subject in need of such treatment a product comprising an anti-inflammatory agent that includes wolfberries or a wolfberry extract in an amount effective to treat inflammation, and milk of animal origin or a carrier containing a milk-protein of animal milk, wherein when a wolfberry extract is used, it has a close profile of the essential active components of whole wolfberries.

2. The method of claim 1, wherein the composition contains a milk selected from the group consisting of cows milk, llama milk, buffalo milk, goat milk, sheep milk, other milk of animal origin and a mixture thereof.

3. The method of claim 1, wherein the primary composition and product exclude insoluble fibers.

4. The method of claim 1, wherein the product is a dietary supplement, a supplement for inclusion in a medicament or pharmaceutical, or a food supplement.

5. The method of claim 3, wherein the primary composition is obtainable by a process comprising the steps of: i) mixing and milling wolfberry material in an animal milk or a milk protein-containing liquid medium from an animal milk, ii) separating insoluble fibers to obtain an aqueous suspension, iii) optionally pasteurising the resulting suspension, iv) optionally adding bioactive components during the processing, v) further optionally drying the suspension to obtain a powder, and vi) formulating the primary composition into a formulation for oral administration.

6. The method of claim 1, wherein the product is a tablet, a capsule, a pill, a solution, a suspension, a syrup, a powder, a gel, a cream, a dried oral supplement, or a wet oral supplement.

7. The method of claim 1, wherein the primary composition comprises at least a part of the lipophilic or hydrophilic bioactive components of wolfberries, wherein the lipophilic or hydrophilic bioactive components are selected from the group consisting of lipids, alkaloid, proteins, carbohydrates, glycoproteins, carotenoids, polyphenolic compounds, flavonoids, vitamins, minerals, and mixtures thereof.

8. The method of claim 7, wherein the glycoproteins are selected from the group consisting of arabinogalactan proteins, *Lycium barbarum* polysaccharides, macromolecules that can be detected by the beta-glucosyl Yariv reagent, and mixtures thereof; or wherein the flavonoids are selected from the group consisting of apigenin, luteolin diosmetin or other flavols, quercetin, myricetin, kaempferol, or other flavonols, flavanones, pelargonidin, malvidin, or other anthocyanidins, genistein, daidzein, or other isoflavones, and mixtures thereof; or the carotenoids are selected from the group consisting of carotenes, xanthophylls, lycopene, carotene, phytofluene, phytoene, canthaxanthin, betacryptoxanthin, capsanthin, lutein, zeaxanthin, the previous compounds in the form of fatty acid esters, and mixtures thereof.

9. The method of claim 1, wherein the inflammation is selected from the group consisting of UV or chemical-induced skin inflammation, eczema, reactive skin, psoriasis, vitiligo, acne, atopic dermatitis and skin imperfections.

10. The method of claim 1, wherein the product is administered to the subject in an amount sufficient to boost the immune system, to improve an impaired immune response, to enhance an antigen-specific humoral immune response, or to enhance cell mediated immune response.

11. The method of claim 1, wherein the primary composition is obtainable by a process comprising the steps of: i) mixing and milling wolfberry material in the animal milk or milk protein-containing liquid medium from animal milk, ii) optionally separating insoluble fibers to obtain an aqueous suspension, iii) optionally pasteurising the resulting suspension, iv) optionally adding bioactive components during the processing, v) further optionally drying the suspension to obtain a powder, and vi) formulating the primary composition into a formulation for oral administration.

12. A method for treating oxidative stress, the method comprising:
orally administering to an elderly subject in need of such treatment a product comprising an anti-inflammatory agent that includes wolfberries or a wolfberry extract in an amount effective to treat oxidative stress, and milk of animal origin or a carrier containing a milk-protein of animal milk, wherein when a wolfberry extract is used, it has a close profile of the essential active components of whole wolfberries.

13. The method of claim 12, wherein the composition contains a milk selected from the group consisting of cows milk, llama milk, buffalo milk, goat milk, sheep milk, other milk of animal origin and a mixture thereof.

14. The method of claim 12, wherein the primary composition and product exclude insoluble fibers.

15. The method of claim 12, wherein the primary composition comprises at least a part of the lipophilic or hydrophilic bioactive components of wolfberries, wherein the lipophilic or hydrophilic bioactive components are selected from the group consisting of lipids, alkaloid, proteins, carbohydrates, glycoproteins, carotenoids, polyphenolic compounds, flavonoids, vitamins, minerals, and mixtures thereof.

16. The method of claim 14, wherein the primary composition is obtainable by a process comprising the steps of: i) mixing and milling wolfberry material in an animal milk or a milk protein-containing liquid medium from an animal milk, ii) separating insoluble fibers to obtain an aqueous suspension, iii) optionally pasteurising the resulting suspension, iv) optionally adding bioactive components during the processing, v) further optionally drying the suspension to obtain a powder, and formulating the primary composition into a formulation for oral administration.

17. The method of claim 12, wherein the product is administered to the subject in an amount sufficient to boost the immune system, to improve an impaired immune response, to enhance an antigen-specific humoral immune response, or to enhance cell mediated immune response.

18. The method of claim 12, wherein the primary composition is obtainable by a process comprising the steps of: i) mixing and milling wolfberry material in the animal milk or milk protein-containing liquid medium from animal milk, ii) optionally separating insoluble fibers to obtain an aqueous suspension, iii) optionally pasteurising the resulting suspension, iv) optionally adding bioactive components during the processing, v) further optionally drying the suspension to obtain a powder, and vi) formulating the primary composition into a formulation for oral administration.

* * * * *